(12) United States Patent
Chorghade et al.

(10) Patent No.: US 6,861,532 B2
(45) Date of Patent: Mar. 1, 2005

(54) SYNTHESIS OF 2-ALKYLCYSTEINE

(75) Inventors: Mukund S. Chorghade, Natick, MA (US); Mukund K. Gurjar, Pune Maharashtra (IN); Bhanu M. Chanda, Pune Maharashtra (IN); Joseph Cherian, Kerala (IN)

(73) Assignee: Genzyme Corporation, Cambridge, MA (US)

(*) Notice: Subject to any disclaimer, the term of this patent is extended or adjusted under 35 U.S.C. 154(b) by 0 days.

(21) Appl. No.: 10/438,745

(22) Filed: May 15, 2003

(65) Prior Publication Data

US 2003/0229231 A1 Dec. 11, 2003

Related U.S. Application Data

(60) Provisional application No. 60/381,012, filed on May 15, 2002, provisional application No. 60/381,021, filed on May 15, 2002, provisional application No. 60/380,894, filed on May 15, 2002, provisional application No. 60/380,910, filed on May 15, 2002, provisional application No. 60/380,880, filed on May 15, 2002, provisional application No. 60/381,017, filed on May 15, 2002, provisional application No. 60/380,895, filed on May 15, 2002, provisional application No. 60/380,903, filed on May 15, 2002, provisional application No. 60/381,013, filed on May 15, 2002, provisional application No. 60/380,878, filed on May 15, 2002, provisional application No. 60/380,909, filed on May 15, 2002, and provisional application No. 60/392,833, filed on Jun. 27, 2002.

(51) Int. Cl.[7] .................... C07D 277/08; C07C 323/00
(52) U.S. Cl. ........................................ 548/146; 562/557
(58) Field of Search ...................... 548/146; 562/557

(56) References Cited

U.S. PATENT DOCUMENTS

| | | |
|---|---|---|
| 4,406,905 A | 9/1983 | Zähner et al. |
| 5,554,753 A | 9/1996 | O'Donnell et al. |
| 5,840,739 A | 11/1998 | Bergeron, Jr. |
| 5,872,259 A | 2/1999 | Reuter |
| 5,929,232 A | 7/1999 | Jacobsen et al. |
| 6,083,966 A | 7/2000 | Bergeron, Jr. |
| 6,159,983 A | 12/2000 | Bergeron, Jr. |
| 6,383,233 B1 | 5/2002 | Reuter |
| 6,428,583 B1 | 8/2002 | Reuter |
| 6,521,652 B1 | 2/2003 | Bergeron |
| 6,525,080 B1 | 2/2003 | Bergeron |
| 6,559,315 B1 | 5/2003 | Bergeron |
| 2003/0088105 A1 | 5/2003 | Krich et al. |
| 2003/0220504 A1 | 11/2003 | Chorghade et al. |
| 2003/0225287 A1 | 12/2003 | Chorghade et al. |
| 2003/0236404 A1 | 12/2003 | Gimi et al. |
| 2003/0236426 A1 | 12/2003 | Chorghade et al. |
| 2003/0236434 A1 | 12/2003 | Gimi et al. |
| 2003/0236435 A1 | 12/2003 | Gimi et al. |
| 2004/0002613 A1 | 1/2004 | Chorghade et al. |
| 2004/0006224 A1 | 1/2004 | Chorghade et al. |
| 2004/0024224 A1 | 2/2004 | Chorghade et al. |

FOREIGN PATENT DOCUMENTS

| | | |
|---|---|---|
| DE | 20 20 866 A | 11/1971 |
| DE | 30 02 989 A1 | 7/1981 |
| EP | 1 302 467 A2 | 4/2003 |
| GB | 1 292 170 | 10/1972 |
| WO | WO 94/11367 | 5/1994 |
| WO | WO 97/36885 | 10/1997 |
| WO | WO 00/01670 | 1/2000 |
| WO | WO 00/12493 | 3/2000 |
| WO | WO 00/16763 | 3/2000 |

OTHER PUBLICATIONS

Bergeron et al, Journal of Medicinal Chemistry, Effects of C–4 Stereochemistry and C–4' Hydroxylation on the Iron Clearing Efficiency and Toxicity of Desferrithiocin Analogues, 1999, 42 pages 2432–2440.*

House, Modern Synthetic Reactions, 2nd edition, 1972, W. A. Benjamin, Inc., London, pp. 546–547.*

Ehrler, Juerg, and Farooq, Saleem, "Total Synthesis of Thiangazole," *Synlett,* 702–704 (1994).

Kishore, V., et al., "Synthesis of α–Poly–[$N^\epsilon$–(2–aryl–$\Delta^2$–thiazoline–4–carbonyl)–$_L$–lysines] With Antiviral Activity," *Indian Journal of Chemistry 15B:* 255–257 (1977).

Zamri, Adel, and Abdallah, Mohamed A., "An Improved Stereocontrolled Synthesis of Pyochelin, Siderophore of *Pseudomonas aeruginosa* and *Burkholderia cepacia,*" *Tetrahedron 56:* 249–256 (2000).

Bergeron, R., et al., "Desazadesmethyldesferrithiocin Analogues as Orally Effective Iron Chelators," *J. Med. Chem.,* 42:95–108 (1999).

Bergeron, R. et al., "The Desferrithiocin Pharmacophore," *J. Med. Chem.,* 37:1411–1417 (1994).

Bergeron, R. et al., "Effects of C–4 Stereochemistry and C–4 Hydroxylation on the Iron Clearing Efficiency and Toxicity of Desferrithiocin Analogues," *J. Med. Chem.,* 42:2432–2440 (1999).

(List continued on next page.)

*Primary Examiner*—Paul A. Zucker
(74) *Attorney, Agent, or Firm*—Hamilton, Brook, Smith & Reynolds, P.C.

(57) ABSTRACT

Non-natural amino acids such as 2-alkylated amino acids allow for the synthesis of a wider variety of peptidal and non-peptidal pharmaceutically active agents. A method of preparing a 2-alkylcysteine involves condensing cysteine with an aryl nitrile to form a 2-arylthiazoline-4-carboxylic acid, followed by alkylating the 2-arylthiazoline-4-carboxylic acid at the 4-position. The present invention also discloses a method of preparing a class of iron chelating agents related to desferrithiocin, all of which contain a thiazoline ring. In this method, an aryl nitrile or imidate is condensed with cysteine or a 2-alkyl cysteine.

10 Claims, No Drawings

OTHER PUBLICATIONS

Bergeron, R. et al., "Synthesis and Biological Evaluation of Naphthyldesferrithiocin Iron Chelators," *J. Med. Chem.,* 39:1575–1581 (1996).

Bergeron, R. et al., "Evaluation of Desferrithiocin and Its Synthetic Analogues as Orally Effective Iron Chelators," *J. Med. Chem.,* 34:2072–2078 (1991).

Bergeron, R. et al., "Evaluation of the Desferrithiocin Pharmacophore as a Vector for Hydroxamates," *J. Med. Chem.,* 42:2881–2886 (1999).

Bergeron, R. et al., "An Investigation of Desferrithiocin Metabolism," *J. Med. Chem.,* 37:2889–2895 (1994).

Bergeron, R. et al., "A Comparative Study of the Iron–Clearing Properties of Desferrithiocin Analogues with Desferrioxamine B in a *Cebus* Monkey Model," *Blood,* 81(8):2166–2173 (1993).

Bergeron, R. et al., "Pharmacokinetics of Orally Administered Desferrithiocin Analogs in *Cebus Apella* Primates," *Drug Metabolism and Disposition,* 27(12):1496–1498 (1999).

Mulqueen, G. C., et al., "Synthesis of the Thiazoline–based Siderophore (S)–Desferrithiocin," *Tetrahedron,* 49(24):5359–5364 (1993).

O'Donnell, M. J., et al., "α–Methyl Amino Acids by Catalytic Phase–Transfer Aklylations," *Tetrahedron Letters,* 23(41):4259–4262 (1982).

* cited by examiner

SYNTHESIS OF 2-ALKYLCYSTEINE

RELATED APPLICATIONS

This application claims the benefit of U.S. Provisional Application Nos. 60/381,012, 60/381,021, 60/380,894, 60/380,910, 60/380,880, 60/381,017, 60/380,895, 60/380,903, 60/381,013, 60/380,878 and 60/380,909, all of which were filed May 15, 2002. This application also claims the benefit of U.S. Provisional Application No. 60/392,833, filed Jun. 27, 2002. The entire teachings of the above-referenced applications are incorporated herein by reference.

BACKGROUND OF THE INVENTION

Alpha-amino acids are useful starting materials in the synthesis of peptides, as well as non-peptidal, pharmaceutically active peptidomimetic agents. In order to enable the synthesis of a large number of compounds from an amino acid precursor, it is advantageous to have naturally occurring and non-naturally occurring amino acids. Non-naturally occurring amino acids typically differ from natural amino acids by their stereochemistry (e.g., enantiomers), by the addition of alkyl groups or other functionalities, or both. At this time, the enantiomers of naturally occurring amino acids are much more expensive than the naturally occurring amino acids. In addition, there are only a limited number of commercially available amino acids that are functionalized or alkylated at the alpha-carbon, and often syntheses involve the use of pyrophoric or otherwise hazardous reagents. Moreover, the syntheses are often difficult to scale up to a commercially useful quantity. Consequently, there is a need for new methodologies of producing such non-naturally occurring amino acids.

Non-naturally occurring amino acids of interest include the (R)- and (S)-isomers of 2-methylcysteine, which are used in the design of pharmaceutically active moieties. Several natural products derived from these isomers have been discovered in the past few years. These natural products include desferrithiocin, from *Streptomyces antibioticus*; as well as tantazole A, mirabazole C, and thiangazole, all from blue-green algae. These compounds have diverse biological activities ranging from iron chelation to murine solid tumor-selective cytotoxicity to inhibition of HIV-1 infection.

Desferrithiocin, deferiprone, and related compounds represent an advance in iron chelation therapy for subjects suffering from iron overload diseases. Present therapeutic agents such as desferroxamine require parenteral administration and have a very short half-life in the body, so that patient compliance and treatment cost are serious problems for subjects receiving long-term chelation therapy. Desferrithiocin and related compounds are effective when orally administered, thereby reducing patient compliance issues. Unfortunately, (S)-2-methylcysteine, which is a precursor to the more active forms of desferrithiocin and related compounds, remains a synthetic challenge. Therefore, there is a need for novel methods of producing 2-methylcysteine at a reasonable cost, and means of isolating the desired enantiomer.

SUMMARY OF THE INVENTION

The present invention includes a method of preparing a 2-alkylated cysteine represented by Structural Formula (I):

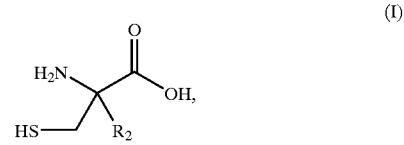

(I)

or salts thereof;

wherein $R_2$ is a substituted or unsubstituted alkyl group; comprising the steps of:

a.) reacting a compound represented by Structural Formula (II):

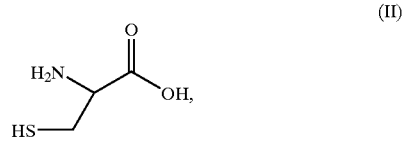

(II)

with a substituted or unsubstituted aryl nitrile of the formula Ar—CN, wherein Ar is a substituted or unsubstituted aryl group; thereby forming a substituted thiazoline represented by Structural Formula (III):

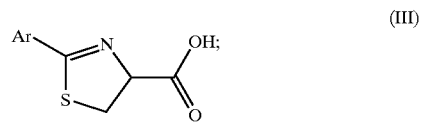

(III)

b.) alkylating the substituted thiazoline with one or more bases and $R_2X$, wherein X is a leaving group and $R_2$ is as defined above; thereby forming an alkylated substituted thiazoline represented by Structural Formula (IV):

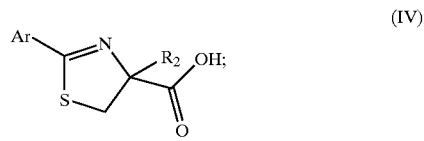

(IV)

c.) reacting the alkylated substituted thiazoline with acid (preferably an inorganic acid such as HCl, HBr or sulfuric acid), thereby forming the 2-alkylated cysteine represented by Structural Formula (I).

The present invention also includes a method of preparing a compound represented by Structural Formula (V):

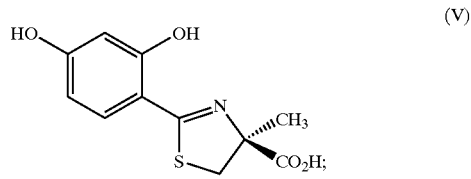

(V)

comprising the steps of:

a.) reacting a compound represented by Structural Formula (II):

(II)

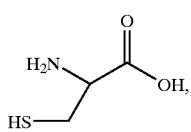

with a substituted or unsubstituted aryl nitrile of the formula Ar—CN, wherein Ar is a substituted or unsubstituted aryl group; thereby forming a substituted thiazoline represented by Structural Formula (III):

(III)

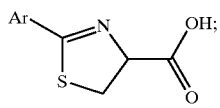

b.) alkylating the substituted thiazoline with one or more bases and $CH_3X$, wherein X is a leaving group; thereby forming an alkylated substituted thiazoline represented by Structural Formula (IV):

(IV)

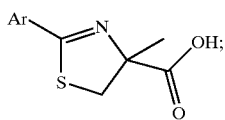

c.) resolving the alkylated substituted thiazoline into (R)-4-methyl-2-arylthiazoline-4-carboxylic acid and (S)-4-methylthiazoline-4-carboxylic acid;

d.) isolating (S)-4-methyl-2-arylthiazoline-4-carboxylic acid;

e.) reacting (S)-4-methyl-2-arylthiazoline-4-carboxylic acid with acid, thereby forming (S)-2-methylcysteine; and f.) coupling (S)-2-methylcysteine with 2,4-dihydroxybenzonitrile, thereby forming the compound represented by Structural Formula (V).

In another embodiment, an analogous compound to that shown in the previous embodiment can be synthesized by coupling 2-hydroxybenzonitrile and (S)-2-methylcysteine or a salt or an ester thereof. Similar syntheses can be conducted with other substituted benzonitriles.

Advantages of the present invention include the facile synthesis of a 2-alkyl cysteine from cysteine, an inexpensive and readily available starting material. 2-Methylcysteine prepared by the method of the present invention can be coupled to 2,4-dihydroxybenzonitrile to form 4'-hydroxydesazadesferrithiocin, also referred to as 4,5-dihydro-2-(2,4-dihydroxyphenyl)-4-methylthiazole-4(S)-carboxylic acid, an iron chelating agent.

DETAILED DESCRIPTION OF THE INVENTION

A useful and efficient method of preparing 2-alkylcysteine involves condensing cysteine with an aryl nitrile to form a 2-arylthiazoline-4-carboxylic acid, followed by alkyation at the 4-position of the thiazoline ring. The resulting racemic 2-alkylcysteine product can be resolved and isolated into a pure or substantially pure enantiomer by a number of methods.

The condensation of an aryl nitrile and cysteine typically occurs in a polar, protic solvent (e.g., water, methanol, ethanol, formamide, formic acid, acetic acid, dimethylformamide, N-ethylacetamide, formaldehyde diethyl acetal) in the presence of an excess of base. Typically, the aryl nitrile and cysteine are refluxed together for several hours, such as 1–20 hours, 2–15 hours, 4–10 hours, or 6–8 hours. Refluxing preferably occurs in an inert atmosphere, such as nitrogen or argon. An alcohol such as methanol or ethanol is a preferred solvent. Preferred aryl nitriles include aryl nitriles where the aryl group is a substituted or unsubstituted phenyl group. Phenyl is a preferred aryl group. Suitable bases include secondary and tertiary amines such as dimethylamine, diethylamine, trimethylamine, diphenylamine, diisopropylamine, diisopropylethylamine, 1,4-diazabicyclo[2.2.2]octane (DABCO), 1,5-diazabicyclo[4.3.0]non-5-ene (DBN), and triethylamine. Suitable amounts of base have at least about one equivalent of base, and range from about 1 to about 10, about 1 to about 5, about 1 to about 3, and about 1 to about 2 equivalents, relative to the amount of cysteine.

Alternatively, an aryl imidate (e.g., a benzimidate, where the benzene ring can have one or more substituents, as described below) can be condensed with cysteine. Typically, the aryl imidate is reacted with cysteine under basic conditions. Acceptable bases include those named above. Aryl imidates can be prepared, for example, for aryl nitriles, aryl carboxylic acids, and aryl amides. Examples of aryl imidate preparation can be found, for example, in U.S. application No. 60/380,909, filed May 15, 2002, the contents of which are incorporated herein by reference. In one example, an aryl carboxylic acid (e.g., benzoic acid) is converted into an acid chloride, then an amide, followed by reaction with a trialkyloxonium hexafluorophosphate or a trialkyloxonium tetrafluoroborate to form the aryl imidate. In a second example, an aryl nitrile is converted into an aryl imidate through reaction with an alcohol in the presence of an acid, as is described below.

The 2-arylthiazoline-4-carboxylic acid can be alkylated in the presence of one or more bases, an alkylating agent, and optionally a phase transfer catalyst. Typically, the 2-arylthiazoline-4 carboxylic acid is reacted with one or more equivalents (e.g., about 1 to about 10 equivalents, about 1 to about 5 equivalents, about 1 to about 3 equivalents, or about 1.5 to about 2.5 equivalents) of base and one or more equivalents (e.g., about 1 to about 5 equivalents, about 1 to about 2 equivalents, about 1 to about 1.5 equivalents, about 1 to about 1.1 equivalents) of an alkylating agent in a polar, aprotic solvent (e.g., acetone, acetonitrile, dimethylformamide, dioxane, ethyl acetate, ethyl ether, hexamethylphosphoramide, tetrahydrofuran) at about −80° C. to about 40° C., about −50° C. to about 25° C., about −20° C. to about 10° C., or about −5° C. to about 5° C. Alkylating agents are of the formula $R_2X$, where $R_2$ and X are as defined above. Preferred $R_2$ groups include substituted or unsubstituted C1–C4 alkyl groups; methyl and benzyl are preferred $R_2$. The leaving group X is typically a weak base. Suitable leaving groups include halogen, tosyl, triflyl, brosyl, p-nitrophenyl, 2,4-dinitrophenyl, and mesyl groups. Halogens include bromine, chlorine, and iodine. Iodine is a preferred leaving group. Preferred bases include potassium t-butoxide, sodium methoxide, sodium ethoxide, sodium amide, and other alkali and alkaline earth metal alkoxides.

Examples of phase transfer catalysts include benzyl triethyl ammonium chloride, benzyl trimethyl ammonium chloride, benzyl tributyl ammonium chloride, tetrabutyl ammonium bromide, tetraethyl ammonium bromide, tetrabutyl ammonium hydrogen sulfate, tetramethyl ammonium iodide, tetramethyl ammonium chloride, triethylbutyl ammonium bromide, tributyl ethyl ammonium bromide, tributyl methyl ammonium chloride, 2-chloroethylamine chloride HCl, bis(2-chloroethyl)amine HCl, 2-dimethylaminoethyl chloride HCl, 2-ethylaminoethyl chloride HCl, 3-dimethylaminopropyl chloride HCl, methylamine HCl, dimethylamine HCl, trimethylamine HCl, monoethylamine HCl, diethylamine HCl, triethylamine HCl, ethanolamine HCl, diethanolamine HCl, triethanolamine HCl, cyclohexylamine HCl, dicyclohexylamine HCl, cyclohexylamine HCl, diusopropylethylamine HCl, ethylenediamine HCl, aniline HCl, methyl salicylate, ethyl salicylate, butyl salicylate amyl salicylate, isoamyl salicylate, 2-ethylsalicylate, and benzyl salicylate.

In a preferred embodiment of the present invention, enantiomers of an alkylated substituted thiazoline are resolved. The alkylated substituted thiazoline can be resolved by emulsion crystallization or by reacting the alkylated substituted thiazoline with one enantiomer of a 1-alkyl-1-aminoalkane or a 1-aryl-1-aminoalkane (i.e., to form a diastereomeric salt). Resolution of chiral compounds using diastereomeric salts is further described in *CRC Handbook of Optical Resolutions via Diastereomeric Salt Formation* by David Kozma (CRC Press, 2001), which is incorporated herein by reference in its entirety. Following resolution, the (R) enantiomer or, preferably, the (S) enantiomer of the alkylated substituted thiazoline is isolated. The enantiomer is subsequently hydrolyzed with an acid (e.g., HCl, HBr, dilute $H_2SO_4$) to obtain, for example, a (S)-2-alkylcysteine. Alternatively, the alkylated substituted thiazoline can first be hydrolyzed with acid to form an amino acid and the resultant amino acid can be resolved by, for example, one of the above-named methods.

When forming a diastereomeric salt, suitable chiral amines include arylalkylamines such as 1-alkyl-1-aminoalkanes and 1-aryl-1-aminoalkanes. Examples include (R)-1-phenylethylamine, (S)-1-phenylethylamine, (R)-1-tolylethylamine, (S)-1-tolylethylamine, (R)-1-phenylpropylamine, (S)-1-propylamine, (R)-1-tolylpropylamine, and (S)-1-tolylpropylamine.

Diastereomers or entantiomers of amino acids or functionalized derivatives thereof (e.g., esters) can also be resolved by emulsion crystallization. Emulsion crystallization is described in U.S. Pat. Nos. 5,872,259, 6,383,233 and 6,428,583, which are incorporated herein by reference. Briefly, emulsion crystallization is a process for separating a desired substance from an aggregate mixture. The process involves forming a three phase system, the first phase comprising the aggregate mixture, the second phase being liquid and comprising a transport phase, and the third phase comprising a surface upon which the desired substance can crystallize. A chemical potential exists for crystal growth of the desired substance in the third phase of the system, thereby creating a flow of the desired substance from the first phase through the second phase to the third phase, where the desired substance crystallizes and whereby an equilibrium of the activities of the remaining substances in the aggregate mixture is maintained between the first phase and the second phase.

In one example of emulsion crystallization, a solution of the racemic mixture is supersaturated (by either cooling, adding a solvent in which one or more components are sparingly soluble or by evaporation of the solution). Ultrasonication eventually helps the process of forming an emulsion. The mixture is then seeded with crystals of the desired, optically active acid along with an additional quantity of surfactant and an anti-foaming agent. The desired product usually crystallizes out and can be separated by filtration. Further details of emulsion crystallization for an amino acid derivative can be found in Example 4.

Cysteine or a 2-alkylcysteine such as (S)-2-methylcysteine can be coupled to a substituted or unsubstituted aryl nitrile such as a substituted or unsubstituted benzonitrile. Preferably, the substituents on benzonitrile will not interfere with the coupling reaction. In a preferred embodiment, (S)-2-methylcysteine is coupled to 2,4-dihydroxybenzonitrile to form 4,5-dihydro-2-(2,4-dihydroxyphenyl)-4-methylthiazole-4(S)-carboxylic acid (also known as 4'-hydroxydesazadesferrithiocin).

Typically, coupling of cysteine or a 2-alkylcysteine and a substituted or unsubstituted benzonitrile includes converting the benzonitrile into a benzimidate. The benzimidate can be formed, for example, by reacting the benzonitrile with an alcohol such as methanol, ethanol, n-propanol, or isopropanol in the presence of an acid such as hydrochloric acid. Alternatively, cysteine or a related compound can be coupled directly with a benzimidate. The benzimidate is then reacted with the cysteine (or related compound) under basic conditions. Acceptable bases include those listed above. The reaction between the benzimidate and the cysteine results in the thiazoline (or 4,5-dihydrothiazole) containing product. When forming the benzimidate from a hydroxylated benzonitrile (e.g., 2,4-dihydroxybenzonitrile), the hydroxyl groups are advantageously protected (e.g., with a substituted or unsubstituted alkyl or arylalkyl group such as a benzyl group). The protecting groups are subsequently cleaved, typically by catalytic hydrogenation.

The methods of the claimed invention can be used to manufacture other related desferrithiocin analogs and derivatives. Examples of such analogs include those described in U.S. Pat. Nos. 5,840,739, 6,083,966, 6,159,983, 6,521,652 and 6,525,080 to Raymond J. Bergeron, Jr., the contents of which are incorporated herein by reference. Additional examples can be found in PCT/US93/10936, PCT/US97/04666, and PCT/US99/19691, the contents of which are incorporated by reference.

Suitable benzonitriles and benzimidates for use in the above coupling reaction can be synthesized by methods described in U.S. application Nos. 60/381,013, 60/380,878 and 60/380,909, filed May 15, 2002, the entire teachings of which are incorporated herein by reference.

An alkyl group is a hydrocarbon in a molecule that is bonded to one other group in the molecule through a single covalent bond from one of its carbon atoms. Alkyl groups can be cyclic or acyclic, branched or unbranched, and saturated or unsaturated. Typically, an alkyl group has one to about 24 carbons atoms, or one to about 12 carbon atoms.

Lower alkyl groups have one to four carbon atoms and include methyl, ethyl, n-propyl, iso-propyl, n-butyl, sec-butyl and tert-butyl.

Aromatic (or aryl) groups include carbocyclic aromatic groups such as phenyl, p-tolyl, 1-naphthyl, 2-naphthyl, 1-anthracyl and 2-anthracyl. Aromatic groups also include heteroaromatic groups such as N-imidazolyl, 2-imidazole, 2-thienyl, 3-thienyl, 2-furanyl, 3-furanyl, 2-pyridyl, 3-pyridyl, 4-pyridyl, 2-pyrimidyl, 4-pyrimidyl, 2-pyranyl, 3-pyranyl, 3-pyrazolyl, 4-pyrazolyl, 5-pyrazolyl, 2-pyrazinyl, 2-thiazolyl, 4-thiazolyl, 5 -thiazolyl, 2-oxazolyl, 4-oxazolyl and 5-oxazolyl.

Aromatic groups also include fused polycyclic aromatic ring systems in which a carbocyclic, alicyclic, or aromatic ring or heteroaryl ring is fused to one or more other heteroaryl or aryl rings. Examples include 2-benzothienyl, 3-benzothienyl, 2-benzofuranyl, 3-benzofuranyl, 2-indolyl, 3-indolyl, 2-quinolinyl, 3-quinolinyl, 2-benzothiazole, 2-benzooxazole, 2-benzimidazole, 2-quinolinyl, 3-quinolinyl, 1-isoquinolinyl, 3-quinolinyl, 1-isoindolyl and 3-isoindolyl.

Suitable substituents for alkyl groups include —OH, halogen (—Br, —Cl, —I and —F), —O(R'), —O—CO—(R'), —CN, —NO$_2$, —COOH, =O, —NH$_2$, —N-H(R'), —N(R')$_2$, —COO(R'), —CONH$_2$, —CONH(R'), —CON(R')$_2$, —SH, —S(R'), and guanidine. Each R' is independently an alkyl group or an aryl group. Alkyl groups can additionally be substituted by a aryl group (e.g. an alkyl group can be substituted with an aromatic group to form an arylalkyl group). A substituted alkyl group can have more than one substituent.

Suitable substituents for aryl groups include —OH, halogen (—Br, —Cl, —I and —F), —O(R'), —O—CO—(R'), —CN, —NO$_2$, —COOH, =O, —NH$_2$, —NH(R'), —N(R')$_2$, —COO(R'), —CONH$_2$, —CONH(R'), —CON(R')$_2$, —SH, —S(R'), and guanidine. Each R' is independently an alkyl group or an aryl group. Aryl groups can additionally be substituted by an alkyl or cycloaliphatic group (e.g. an aryl group can be substituted with an alkyl group to form an alkylaryl group such as tolyl). A substituted aryl group can have more than one substituent.

Also included in the present invention are salts of the disclosed amino acids. For example, amino acids can also be present in the anionic, or conjugate base, form, in combination with a cation. Suitable cations include alkali metal ions, such as sodium and potassium ions, alkaline earth ions, such as calcium and magnesium ions, and unsubstituted and substituted (primary, secondary, tertiary and quaternary) ammonium ions. Suitable cations also include transition metal ions such as manganese, copper, nickel, iron, cobalt, and zinc. Basic groups such as amines can also be protonated with a counter anion, such as hydroxide, halogens (chloride, bromide, and iodide), acetate, formate, citrate, ascorbate, sulfate or phosphate.

EXAMPLE 1

Cysteine, benzonitrile, and 5 equivalents of triethylamine were refluxed in ethanol for 6–8 hours to obtain a 66–70% yield of 2-phenylthiazoline-4-carboxylic acid. The 2-phenylthiazoline-4 carboxylic acid was reacted with 2.05 equivalents of base and 1 equivalent of methyl iodide in tetrahydrofuran at 0° C. to form 2-phenyl-4-methylthiazoline-4 carboxylic acid. The 2-phenyl-4-methylthiazoline-4 carboxylic acid can be resolved and isolated as the (S)-enantiomer using emulsion crystallization, and subsequently hydrolyzed with hydrochloric acid, thereby obtaining (S)-2-methylcysteine hydrochloride.

EXAMPLE 2

Cysteine, benzonitrile, and 5 equivalents of triethylamine were refluxed in ethanol for 6–8 hours to obtain a 66–70% yield of 2-phenylthiazoline-4-carboxylic acid. The 2-phenylthiazoline-4 carboxylic acid was reacted with 2.05 equivalents of base and 1 equivalent of methyl iodide in tetrahydrofuran at 0° C. to form 2-phenyl-4-methylthiazoline-4 carboxylic acid. The 2-phenyl-4-methylthiazoline-4-carboxylic acid can be hydrolyzed with hydrochloride acid, thereby obtaining a mixture of (R)- and (S)-2-methylcysteine hydrochloride.

EXAMPLE 3

The procedure of Example 2 is followed, such that a mixture of (R)- and (S)-2-methylcysteine hydrochloride is obtained. Classical chemical resolution with (R)-phenylethylamine at a suitable pH is able to resolve the (R)- and (S)-enantiomers of 2-methylcysteine. Subsequent isolation of the resolved products yields substantially enantiomerically pure (R)-2-methylcysteine and (S)-2-methylcysteine.

EXAMPLE 4

All compounds were used without further purification. The surfactants Rhodafac RE 610 and Soprophor FL were obtained from Rhône-Poulenc, Surfynol 465 from Air Products, Synperonic NP 10 from ICI and sodium lauryl sulfate from Fluka. For agitation a shaking machine was used (Buhler KL Tuttlingen). Purities of the resulting crystals were measured by using a PolarMonitor polarimeter (IBZ Hannover). Ethanol was used as the solvent. The total crystal quantity was dissolved in a 1 mL cell at 20° C.).

45 mg of (R,R)- and (S,S)-amino acid derivatives were dissolved in 1 ml of a mixture of 20% v/v 2-hexanol, 12% v/v Rhodafac RE 610, 6% v/v Soprophor FL and 62% v/v water by heating to 80° C. in a 5 mL vial. After the organic derivative was completely dissolved the microemulsion was cooled down to room temperature and agitated using a shaking machine (420 rpm). During two hours no spontaneous crystallization was observed. The mixture was then seeded with two drops of a dilute, finely ground suspension of pure (S,S)-(−) amino acid or its ester crystals grown under similar conditions. After 2 hours of agitation the resulting crystals were filtered off, washed with water and dried in a gentle nitrogen stream.

EXAMPLE 5

35 mg of R- and S-4,5-dihydro-2-(2,4-dihydroxyphenyl)-4-methylthiazole-4-carboxylic acid were dissolved in 1 ml of a mixture of 9% N-methyl-pyrrolidone, 9% v/v 2-hexanol, 10% v/v Rhodafac RE 610, 5% v/v Soprophor FL and 68% v/v water by heating to 50° C. in a 5 mL vial. After the product was completely dissolved, the microemulsion was cooled down to room temperature and agitated with a shaking machine (350 rpm). During two hours, no spontaneous crystallisation was observed. The mixture was then seeded with two drops of a dilute, finely ground suspension of pure S-product crystals grown under similar conditions. After two hours of shaking, the resulting crystals were filtered off, washed with water and dried in a gentle nitrogen stream. The procedure yielded 5.4 mg (15.4%) of colorless crystals, with a greater than 90% purity of the S entantiomer.

EXAMPLE 6

4.00 g (S)-2-methylcysteine hydrochloride (23.3 mmol, 1.0 meq) and 3.14 g 2,4-dihydroxy benzonitrile (23.3 mmol, 1.0 meq) were suspended in 40 mL ethanol. After degassing this mixture with nitrogen (30 min) 4.95 g triethylamine (6.8 mL, 48.9 mmol, 2.05 meq) were added. The obtained suspension was heated under reflux in an atmosphere of nitrogen for 20 hours and then cooled to room temperature. From this suspension ethanol was evaporated under reduced pressure until an oil (20% of the initial volume) was obtained. This oil was dissolved in 50 mL water. The solution was adjusted to pH 7.5 with 1.20 ml 20% KOH and was extracted two times each with 20 mL methyl t-butyl ether (MTBE). The aqueous layer was separated, adjusted with 20% KOH to pH 11 and again extracted two times each with 20 mL MTBE. After separating the aqueous layer the pH was set with concentrated HCl to 7.5 and traces of MTBE were distilled off. Then the aqueous solution was acidified with 1.50 ml concentrated HCl to pH 1.5. The product precipitated. This suspension was stirred at 4° C. for 1 hour. Then the precipitate was filtered, washed two times each with 10 mL water (5° C.) and dried at 45° C. under vacuum. The reaction yielded 5.17 g (87.6%) of crude 4,5-dihydro-2-(2,4-dihydroxyphenyl)-4-methylthiazole-4(S)-carboxylic acid product. $^1$H-NMR showed no significant impurity.

EXAMPLE 7

A single-neck 500 mL round-bottomed flask was flushed with nitrogen. (R)-(+)-L-cysteine hydrochloride monohydrate (12.0 g, 68.32 mmol) was transferred to the flask. Ethanol (240 mL) was added to give a suspension. Anhydrous triethylamine (34.6 g, 47.7 mL, 341.6 mmol, 5.0 equiv.) was then added via a syringe over a period of 10 min. at room temperature. A white precipitate of triethylamine hydrochloride formed immediately. After stirring this thick white turbid solution for 30 min. at room temperature, benzonitrile (7.05 g, 68.32 mmol) was added and the reaction mixture was refluxed for 6 hours. TLC (CH$_2$Cl$_2$ as eluent) indicated that all benzonitrile was consumed. The reaction mixture was cooled to room temperature and the solvent was removed in vacuo. Water (25 mL) was added followed by the addition of solid KOH (5 g) with stirring. This reddish clear aqueous solution (pH~11–12) was extracted with ethyl acetate (3×100 mL) and the organic layer was discarded. The aqueous layer was acidified with dropwise addition of 6M HCl to pH 1.5–2.0 to obtain an off-white to tan colored precipitate. This solid was filtered through a Buchner funnel. After drying under high vacuum, the solid was triturated with ethyl acetate to remove any traces of colored impurities. After filtration and drying, the off-white to white solid was stirred over dichloromethane to remove any traces of triethylamine hydrochloride and then filtered. After drying under vacuum, a white powdery solid was obtained (10.49 g, 74%).

EXAMPLE 8

2,4-Dibenzyloxybenzonitrile (0.121 mol) was dissolved in 5.85 g (0.127 mol) ethanol and 19.4 ml 1,2-dimethoxyethane in a double walled reactor. This solution was cooled to −5° C., stirred and saturated with dry HCl gas over 5 hours at 0–3° C. The reaction mixture was stirred overnight at 2–4° C. under nitrogen. During this time, a product crystallized. The white crystals were filtered off, washed with 1,2-dimethoxyethane (5° C., three times each with 13 ml) and dried. A total of 30 of the protected ethyl benzimidate was isolated (Yield 88.4%, purity 98.9%).

The protected ethyl benzimidate described above was dissolved in methanol to generate a 10% solution and was catalytically hydrogenated at room temperature using 5% Pd/C as a catalyst. The reaction was completed after 8 hours. The solution was filtered and the solvent evaporated to yield the deprotected product as an orange-yellow solid. The reaction yielded 19.6 g (94%) of product.

In contrast, the formation of the imidate with 2,4 dihydroxybenzonitrile was a low yielding process, generating the desired product in only 20% yield and with less than desired purity.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of preparing a 2-alkylated cysteine represented by Structural Formula (I):

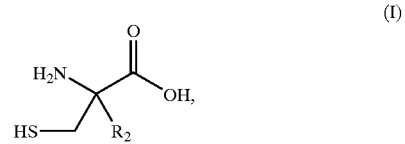

or salts thereof;
wherein $R_2$ is a substituted or unsubstituted alkyl group; comprising the steps of:
a.) reacting a compound represented by Structural Formula (II):

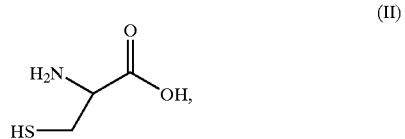

with a substituted or unsubstituted aryl nitrile of the formula Ar—CN in the presence of a secondary or tertiary amine base, wherein Ar is a substituted or unsubstituted aryl group, thereby forming a substituted thiazoline represented by Structural Formula (III):

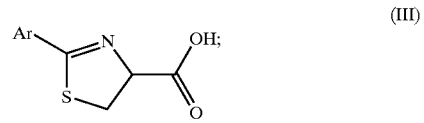

b.) alkylating the substituted thiazoline with one or more bases and $R_2X$, wherein X is a leaving group and $R_2$ is as defined above; thereby forming an alkylated substituted thiazoline represented by Structural Formula (IV):

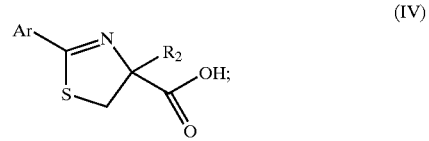

c.) reacting the alkylated substituted thiazoline with acid, thereby forming the 2-alkylated cysteine represented by Structural Formula (I).

2. The method of claim 1, wherein Ar is a substituted or unsubstituted phenyl group.

3. The method of claim 2, wherein $R_2$ is a C1–C4 alkyl group.

4. The method of claim 3, wherein Ar is phenyl.

5. The method of claim 4, wherein the one or more bases of step b.) are selected from the group consisting of potassium t-butoxide, sodium methoxide, sodium ethoxide, and sodium amide.

6. The method of claim 5, wherein X is iodine.

7. The method of claim 6, wherein $R_2$ is methyl.

8. The method of claim 7, further comprising the step of resolving the enantiomers of the alkylated substituted thiazoline.

9. The method of claim 8, wherein the (S) enantiomer of the alkylated substituted thiazoline is isolated.

10. A method of preparing a compound represented by Structural Formula (V):

(V)

comprising the steps of:

a.) reacting a compound represented by Structural Formula (II):

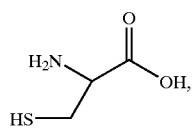
(II)

with a substituted or unsubstituted aryl nitrile of the formula Ar—CN in the presence of a secondary or tertiary amine base, wherein Ar is a substituted or unsubstituted aryl group; thereby forming a substituted thiazoline represented by Structural Formula (III):

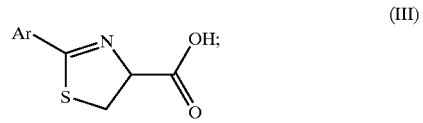
(III)

b.) alkylating the substituted thiazoline with one or more bases and $CH_3X$, wherein X is a leaving group; thereby forming an alkylated substituted thiazoline represented by Structural Formula (IV):

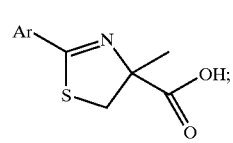
(IV)

c.) resolving the alkylated substituted thiazoline into (R)-4-methyl-2-arylthiazoline-4-carboxylic acid and (S)-4-methyl-2-arylthiazoline-4-carboxylic acid;

d.) isolating (S)-4-methyl-2-arylthiazoline-4-carboxylic acid;

e.) reacting (S)-4-methyl-2-arylthiazoline-4-carboxylic acid with acid, thereby forming (S)-2-methylcysteine; and f.) coupling (S)-2-methylcysteine with 2,4-dihydroxybenzonitrile, thereby forming the compound represented by Structural Formula (V).

* * * * *

UNITED STATES PATENT AND TRADEMARK OFFICE
CERTIFICATE OF CORRECTION

PATENT NO. : 6,861,532 B2
DATED : March 1, 2005
INVENTOR(S) : Mukund S. Chorghade et al.

It is certified that error appears in the above-identified patent and that said Letters Patent is hereby corrected as shown below:

Column 10,
Line 50, insert -- and --.

Signed and Sealed this

Seventeenth Day of January, 2006

JON W. DUDAS
*Director of the United States Patent and Trademark Office*